US012680080B2

(12) United States Patent (10) Patent No.: US 12,680,080 B2
Masuda et al. (45) Date of Patent: Jul. 14, 2026

(54) PROLIFERATIVE LIVER ORGANOID, METABOLICALLY ACTIVATED LIVER ORGANOID, AND USE THEREOF

(71) Applicants: JSR Corporation, Tokyo (JP); KEIO UNIVERSITY, Tokyo (JP)

(72) Inventors: Norio Masuda, Tokyo (JP); Toshiro Sato, Tokyo (JP); Ryo Igarashi, Tokyo (JP)

(73) Assignees: JSR Corporation, Tokyo (JP); KEIO UNIVERSITY, Tokyo (JP)

( * ) Notice: Subject to any disclaimer, the term of this patent is extended or adjusted under 35 U.S.C. 154(b) by 656 days.

(21) Appl. No.: 17/806,398

(22) Filed: Jun. 10, 2022

(65) Prior Publication Data

US 2022/0298485 A1 Sep. 22, 2022

Related U.S. Application Data

(63) Continuation of application No. PCT/JP2020/046781, filed on Dec. 15, 2020.

(30) Foreign Application Priority Data

Dec. 16, 2019 (JP) ................................. 2019-226717

(51) Int. Cl.
*C12N 5/071* (2010.01)
*C12N 5/0735* (2010.01)

(52) U.S. Cl.
CPC ......... *C12N 5/0672* (2013.01); *C12N 5/0606* (2013.01); *C12N 5/0671* (2013.01); *C12N 5/0677* (2013.01); *C12N 5/0679* (2013.01); *C12N 2501/115* (2013.01); *C12N 2501/117* (2013.01); *C12N 2501/12* (2013.01); *C12N 2501/155* (2013.01); *C12N 2501/16* (2013.01); *C12N 2501/39* (2013.01); *C12N 2501/999* (2013.01); *C12N 2503/04* (2013.01); *C12N 2506/02* (2013.01); *C12N 2506/45* (2013.01); *C12N 2510/00* (2013.01); *C12N 2511/00* (2013.01); *C12N 2513/00* (2013.01); *C12N 2533/90* (2013.01)

(58) Field of Classification Search
None
See application file for complete search history.

(56) References Cited

U.S. PATENT DOCUMENTS

2016/0002602 A1 1/2016 Almeida-Porada et al.
2018/0258400 A1 9/2018 Ng et al.
2019/0161734 A1 5/2019 Hu et al.

FOREIGN PATENT DOCUMENTS

CN 110317775 A 10/2019
JP 2013-535201 A 9/2013

| JP | 2014-516562 A | 7/2014 | | |
|----|----|----|----|----|
| JP | 2020-92700 A | 6/2020 | | |
| WO | WO 2012/014076 A2 | 2/2012 | | |
| WO | WO 2012/168930 A2 | 12/2012 | | |
| WO | WO 2015173425 | * 11/2015 | ............. | C12N 5/071 |
| WO | WO 2017/048193 A1 | 3/2017 | | |
| WO | WO 2017149025 | * 9/2017 | ............. | C12N 5/071 |
| WO | WO 2019/222853 A1 | 11/2019 | | |

OTHER PUBLICATIONS

Zhang, Y., Bai, X.F. and Huang, C.X., 2003. Hepatic stem cells: existence and origin. World Journal of Gastroenterology: WJG, 9(2), p. 201-204. (Year: 2003).*
Wang, J., Sun, M., Liu, W., Li, Y. and Li, M., 2019. Stem cell-based therapies for liver diseases: an overview and update. Tissue engineering and regenerative medicine, 16, pp. 107-118. (Year: 2019).*
Kratochvil, M.J., Seymour, A.J., Li, T.L., Pasca, S.P., Kuo, C.J. and Heilshorn, S.C., 2019. Engineered materials for organoid systems. Nature Reviews Materials, 4(9), pp. 606-622. (Year: 2019).*
Hu, H., Gehart, H., Artegiani, B., LÖpez-Iglesias, C., Dekkers, F., Basak, O., van Es, J., de Sousa Lopes, S.M.C., Begthel, H., Korving, J. and van den Born, M., 2018. Long-term expansion of functional mouse and human hepatocytes as 3D organoids. Cell, 175(6), pp. 1591-1606. (Year: 2018).*
Strazzabosco, M. and Fabris, L., 2008. Functional anatomy of normal bile ducts. The Anatomical Record: Advances in Integrative Anatomy and Evolutionary Biology: Advances in Integrative Anatomy and Evolutionary Biology, 291(6), pp. 653-660. (Year: 2008).*
Sun, R., Jaruga, B., Kulkarni, S., Sun, H. and Gao, B., 2005. IL-6 modulates hepatocyte proliferation via induction of HGF/p21cip1: regulation by SOCS3. Biochemical and biophysical research communications, 338(4), pp. 1943-1949. (Year: 2005).*
Arora, M., 2013. Cell culture media: a review. Materials and Methods, 3(175), p. 24. (Year: 2013).*
Rose-John, S., 2018. Interleukin-6 family cytokines. Cold Spring Harbor perspectives in biology, 10(2), p.a028415. (Year: 2018).*
Levy, G., Bomze, D., Heinz, S., Ramachandran, S.D., Noerenberg, A., Cohen, M., Shibolet, O., Sklan, E., Braspenning, J. and Nahmias, Y., 2015. Long-term culture and expansion of primary human hepatocytes. Nature biotechnology, 33(12), pp. 1264-1271. (Year: 2015).*

(Continued)

*Primary Examiner* — Titilayo Moloye
*Assistant Examiner* — Risa Takenaka
(74) *Attorney, Agent, or Firm* — Oblon, McClelland, Maier & Neustadt, L.L.P.

(57) ABSTRACT

A production method for a proliferative liver organoid includes culturing liver stem cells or a tissue fragment including liver stem cells in a growth medium to obtain a proliferative liver organoid, in which the growth medium contains an interleukin-6 family cytokine. A production method for a metabolically activated liver organoid includes culturing the proliferative liver organoid produced by the production method for a proliferative liver organoid in a differentiation medium to obtain a metabolically activated liver organoid, in which the differentiation medium does not substantially contain an interleukin-6 family cytokine.

13 Claims, 3 Drawing Sheets

(56) References Cited

OTHER PUBLICATIONS

Gjorevski, N., Sachs, N., Manfrin, A., Giger, S., Bragina, M.E., Ordóñez-Morán, P., Clevers, H. and Lutolf, M.P., 2016. Designer matrices for intestinal stem cell and organoid culture. Nature, 539(7630), pp. 560-564. (Year: 2016).*

Corning Incorporated, 2017. Corning® Matrigel® Basement Membrane Matrix for 3D Culture In Vitro. (Year: 2017).*

Hui, Q., Jin, Z., Li, X., Liu, C. and Wang, X., 2018. FGF family: from drug development to clinical application. International journal of molecular sciences, 19(7), p. 1875. (Year: 2018).*

International Search Report issued Mar. 2, 2021 in PCT/JP2020/046781, filed on Dec. 15, 2020, 2 pages.

Huch et al., "Long-Term Culture of Genome-Stable Bipotent Stem Cells from Adult Human Liver.", Cell, vol. 160, Jan. 15, 2015, 14 pages.

Hu et al., "Long-Term Expansion of Functional Mouse and Human Hepatocytes as 3D Organoids.", Cell, vol. 175, Nov. 29, 2018, 36 pages.

Michalopoulos, et al., HGF-, EGF-, and Dexamethasone-Induced Gene Expression Patterns During Formation of Tissue in Hepatic Organoid Cultures, Gene Expression, vol. 11, Jan. 28, 2003, 21 pages.

Combined Chinese Office Action and Search Report issued Jul. 18, 2023 in Chinese Application 202080085827.0, (with English translation), 19 pages.

Asai, A. et al., "Paracrine signals regulate human liver organoid maturation from induced pluripotent stem cells," Development, vol. 144, 2017, XP055945850, pp. 1056-1064.

Extended European Search Report issued Dec. 22, 2023 in European Patent Application No. 20903681.3, 10 pages.

* cited by examiner

PASSAGE NUMBER

PROLIFERATIVE LIVER ORGANOID, METABOLICALLY ACTIVATED LIVER ORGANOID, AND USE THEREOF

TECHNICAL FIELD

The present invention relates to a proliferative liver organoid, a metabolically activated liver organoid, and use thereof.

Priority is claimed on Japanese Patent Application No. 2019-226717, filed on Dec. 16, 2019, the content of which is incorporated herein by reference.

BACKGROUND ART

In a pharmacokinetic study in drug development, an in vivo test using a rodent or an in vitro test using (cryopreserved) primary hepatocytes (hepatic parenchymal cells) derived from a rodent is performed. However, it is difficult to predict toxicity specifically generated in humans due to a species difference. Meanwhile, since (cryopreserved) primary human hepatocytes are limited in number, it is difficult to stably procure hepatocytes of good quality.

Drug research and development has progressed by focusing on cytochrome P450 (CYP) that is present in a particularly large amount in hepatocytes in a pharmacokinetic study. CYP is one of main enzymes that metabolize a xenobiotic substance present in the human body. When analyzing drug metabolism carried out by CYP, a human hepatoma-derived cell line called HepaRG (registered trademark, hereinafter, description of "registered trademark" is omitted) developed by the French National Institute of Health and Medical Research (INSERM) is used. HepaRG cells are considered to have a normal CYP activity of human hepatocytes. However, the HepaRG cells require a culturing period for restoration of the CYP activity and are costly to purchase. Furthermore, in a human-derived liver cancer cell line such as HepG2 cells, the CYP activity is low, and toxicity related to metabolism carried out by CYP cannot be evaluated. In addition, use of hepatocytes derived from pluripotent stem cells such as human induced pluripotent stem cells (iPS cells) has also been considered, from the viewpoint of securing a stable number of cells. However, similar to the human-derived liver cancer cell line, the CYP activity is low in the human iPS cell-derived hepatocytes, and a degree of maturation of the cells is also inferior to that of (cryopreserved) primary hepatocytes. For these reasons, human-derived hepatocytes (liver organoid) produced in vitro that can be more stably used are required.

A method of culturing liver organoids from mouse-derived hepatocytes was established by Hans Clevers et al. in 2013, and thereafter, liver organoids were established from human-derived liver stem cells by the same group in 2015. Furthermore, in 2018, liver organoids were established by the same group from liver stem cells of a cellular origin different from that of the above liver organoids, and the liver organoids are anticipated as a new source of hepatocytes (refer to Patent Document 1, Non-Patent Document 1, and Non-Patent Document 2).

CITATION LIST

Patent Literature

[Patent Document 1]
Published Japanese Translation No. 2013-535201 of the PCT International Publication

Non-Patent Literature

[Non-Patent Document 1]
Huch M et al., "Long-term culture of genome-stable bipotent stem cells from adult human liver.", Cell, Vol. 160, Issue 1, pp. 299-312, 2015.
[Non-Patent Document 2]
Hu H et al, "Long-Term Expansion of Functional Mouse and Human Hepatocytes as 3D Organoids.", Cell, Vol. 175, Issue 6, pp. 1591-1606, 2018.

SUMMARY OF INVENTION

Technical Problem

The present invention has been made in view of the above-described circumstances, and an object of the present invention is to provide a proliferative liver organoid which has excellent proliferative properties and a production method therefor, and a metabolically activated liver organoid which is differentiated from the proliferative liver organoid and has an excellent metabolic activity and a production method therefor.

Solution to Problem

That is, the present invention includes the following embodiments.

(1) A production method for a proliferative liver organoid, the production method including:

culturing liver stem cells or a tissue fragment including liver stem cells in a growth medium to obtain a proliferative liver organoid, in which the growth medium contains an interleukin-6 family cytokine.

(2) The production method according to (1), in which the interleukin-6 family cytokine is at least one selected from the group consisting of interleukin-6, interleukin-11, oncostatin M, a leukemia inhibitory factor, cardiotrophin-1, and a ciliary neurotrophic factor.

(3) The production method according to (1) or (2), in which the growth medium does not substantially contain nicotinamide.

(4) The production method according to any one of (1) to (3), in which the growth medium further contains a growth factor.

(5) The production method according to (4), in which the growth factor is at least one selected from the group consisting of an epidermal growth factor, a fibroblast growth factor, a hepatocyte growth factor, amphiregulin, and a heparin-binding EGF-like growth factor.

(6) The production method according to any one of (1) to (5), in which the growth medium further contains a Wnt agonist.

(7) The production method according to (6), in which the Wnt agonist is at least one selected from the group consisting of a Wnt family member, R-spondin 1, R-spondin 2, R-spondin 3, R-spondin 4, norrin, and a glycogen synthase inhibitor.

(8) The production method according to any one of (1) to (7), in which the growth medium further contains a Rho kinase inhibitor.

(9) The production method according to (8), in which the Rho kinase inhibitor is at least one selected from the group consisting of Y-27632, fasudil, Y39983, Wf-536, SLx-2119, azabenzimidazole-aminofurazan, DE-104, H-1152P, a Rho kinase α inhibitor, XD-4000, HMN- 1152, 4-(1-aminoalkyl)-N-(4-pyridyl)cyclohexane-car-boxamide, Rhostatin, BA-210, BA-207, Ki-23095, and VAS-012.

(10) The production method according to any one of (1) to (9), in which the growth medium further contains a transforming growth factor-β inhibitor.

(11) The production method according to (10), in which the transforming growth factor-β inhibitor is at least one selected from the group consisting of A83-01, SB-431542, SB-505124, SB-525334, LY364947, SD-208, and SJN2511.

(12) The production method according to any one of (1) to (11), in which the growth medium further contains a bone morphogenetic protein inhibitor.

(13) The production method according to (12), in which the bone morphogenetic protein inhibitor is at least one selected from the group consisting of noggin, differen-tial screening-selected gene aberrative in neuroblas-toma, Cerberus, and gremlin.

(14) The production method according to any one of (1) to (13), in which the growth medium further contains forskolin.

(15) The production method according to any one of (1) to (14), in which the growth medium further contains at least one selected from the group consisting of gastrin, a neurobiological supplement, and N-acetylcysteine.

(16) The production method according to any one of (1) to (15), in which, in the culturing in the growth medium, the culturing is performed by bringing the liver stem cells or the tissue fragment including liver stem cells and an extracellular matrix into contact with each other.

(17) The production method according to (16), in which, in the culturing in the growth medium, the extracellular matrix is a mixture of collagen and Matrigel.

(18) The production method according to any one of (1) to (17), in which, in the culturing in the growth medium, the culturing is performed for at least two weeks.

(19) A production method for a metabolically activated liver organoid, the production method including:
culturing the proliferative liver organoid produced by the production method according to any one of (1) to (18) in a differentiation medium to obtain a metabolically activated liver organoid,
in which the differentiation medium does not substantially contain an interleukin-6 family cytokine.

(20) The production method according to (19), in which the differentiation medium does not substantially con-tain nicotinamide.

(21) The production method according to (19) or (20), in which the differentiation medium further contains a growth factor.

(22) The production method according to (21), in which the growth factor is at least one selected from the group consisting of an epidermal growth factor, a fibroblast growth factor, and a hepatocyte growth factor.

(23) The production method according to any one of (19) to (22), in which the differentiation medium further contains a Wnt agonist.

(24) The production method according to (23), in which the Wnt agonist is at least one selected from the group consisting of a Wnt family member, R-spondin 1, R-spondin 2, R-spondin 3, R-spondin 4, norrin, and a glycogen synthase inhibitor.

(25) The production method according to any one of (19) to (24), in which the differentiation medium further contains a Rho kinase inhibitor.

(26) The production method according to (25), in which the Rho kinase inhibitor is at least one selected from the group consisting of Y-27632, fasudil, Y39983, Wf-536, SLx-2119, azabenzimidazole-aminofurazan, DE-104, H-1152P, a Rho kinase α inhibitor, XD-4000, HMN-1152, 4-(1-aminoalkyl)-N-(4-pyridyl)cyclohexane-car-boxamide, Rhostatin, BA-210, BA-207, Ki-23095, and VAS-012.

(27) The production method according to any one of (19) to (26), in which the differentiation medium further contains a transforming growth factor-β inhibitor.

(28) The production method according to (27), in which the transforming growth factor-β inhibitor is at least one selected from the group consisting of A83-01, SB-431542, SB-505124, SB-525334, LY364947, SD-208, and SJN2511.

(29) The production method according to any one of (19) to (28), in which the differentiation medium further contains a bone morphogenetic protein inhibitor.

(30) The production method according to (29), in which the bone morphogenetic protein inhibitor is at least one selected from the group consisting of noggin, differen-tial screening-selected gene aberrative in neuroblas-toma, Cerberus, and gremlin.

(31) The production method according to any one of (19) to (30), in which the differentiation medium further contains forskolin.

(32) The production method according to any one of (19) to (31), in which the differentiation medium further contains at least one selected from the group consisting of gastrin, a neurobiological supplement, and N-ace-tylcysteine.

(33) The production method according to any one of (19) to (32), in which the differentiation medium further contains vitamin D.

(34) The production method according to any one of (19) to (33), in which the differentiation medium further contains a Notch inhibitor.

(35) A method of inducing a metabolically activated liver organoid into a proliferative liver organoid, the method including:
culturing the metabolically activated liver organoid pro-duced by the production method according to any one of (19) to (34) in an induction medium to induce the metabolically activated liver organoid into a prolifera-tive liver organoid,
in which the induction medium contains an interleukin-6 family cytokine.

(36) A proliferative liver organoid produced by the pro-duction method according to any one of (1) to (18).

(37) A metabolically activated liver organoid produced by the production method according to any one of (19) to (34).

(38) A growth medium for culturing a proliferative liver organoid, the growth medium including: an inter-leukin-6 family cytokine.

(39) An evaluation method for a test substance, the evaluation method including: bringing the metaboli-cally activated liver organoid according to (37) into contact with a test substance; and evaluating a response of the metabolically activated liver organoid.

Advantageous Effects of Invention

According to the production method for a proliferative liver organoid of the above embodiment, a proliferative liver organoid which has excellent proliferative properties can be provided. According to the production method for a metabolically activated liver organoid of the above embodiment, a metabolically activated liver organoid which is differentiated from the proliferative liver organoid and has an excellent metabolic activity can be provided.

DESCRIPTION OF EMBODIMENTS

Figure 1:
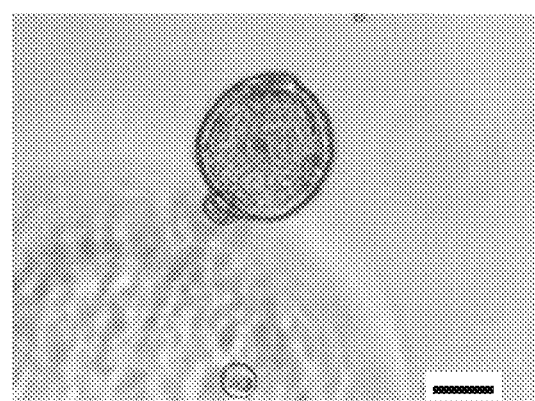
FIG. 1 is a microscope image of proliferative liver organoids in Experimental Example 1. The scale bar is 100 μm.

Hereinafter, the present invention will be further described in detail by presenting embodiments; however, the present invention is not limited to the following embodiments.

Regarding each component exemplified in the present specification, for example, each component in a growth medium or a differentiation medium, one kind of each component can be contained alone, or two or more kinds thereof can be contained in combination, unless otherwise specified.

In the present specification, an expression representing a numerical range such as "A to B" is synonymous with the expression "A or more and B or less" and includes A and B in the numerical range.

<Production Method for Proliferative Liver Organoid>

In one embodiment, the present invention provides a production method for a proliferative liver organoid, the production method including culturing liver stem cells or a tissue fragment including liver stem cells in a growth medium to obtain a proliferative liver organoid (hereinafter, referred to as "Step A"), in which the growth medium contains an interleukin-6 (IL-6) family cytokine.

According to the production method for a proliferative liver organoid of the present embodiment, a proliferative liver organoid having excellent proliferative properties can be obtained.

Since conventional (cryopreserved) primary human hepatocytes are limited in number, it was difficult to stably procure hepatocytes of good quality.

On the other hand, in the production method for a proliferative liver organoid of the present embodiment, a proliferative liver organoid having a proliferative capacity can be obtained from liver stem cells such as (cryopreserved) primary human hepatocytes or a tissue fragment including the liver stem cells. Therefore, hepatocytes of good quality required in a pharmacokinetic study can be stably supplied.

Furthermore, a metabolically activated liver organoid having an excellent metabolic activity is obtained by causing differentiation of the proliferative liver organoid produced by the production method for a proliferative liver organoid of the present embodiment.

The term "metabolically activated liver organoid" in the present specification refers to a cell population having characteristics similar to those of hepatocytes constituting a liver tissue of a living body. Examples of the metabolically activated liver organoid can include a liver organoid in which an albumin expression level is 50% or higher, a CYP2E1 expression level is 300% or higher, a UGT1A1 expression level is 300% or higher, and the NRP2 expression level is 500% or higher, with respect to those in cryopreserved primary human hepatocytes in suspension.

In addition, the expressions "cause differentiation" and "induce differentiation" in the present specification refer to exerting an action so as to cause at least one of complication and acquisition of different characteristics. The differentiation of the proliferative liver organoid into the metabolically activated liver organoid is induced in a production method for a metabolically activated liver organoid of the present embodiment described later.

Note that the "proliferative liver organoid" produced by the production method of the present embodiment and the "metabolically activated liver organoid" produced by the differentiation from the proliferative liver organoid by the production method for a metabolically activated liver organoid of the present embodiment described later may be collectively referred to as a "hepatocyte mass".

[Step A]

In Step A, the liver stem cells or the tissue fragment including liver stem cells are cultured in the growth medium to obtain a proliferative liver organoid.

A liver is composed of hepatic parenchymal cells that are responsible for the essence of liver functions and a hepatic non-parenchymal cell population that supports proliferation and survival of the hepatic parenchymal cells. The hepatic parenchymal cells are also called hepatocytes. The hepatic non-parenchymal cell population includes hepatic stellate cells, sinusoidal endothelial cells, Kupffer cells, biliary epithelial cells, and the like.

The liver stem cells have bipotentiality to differentiate into hepatocytes and biliary epithelial cells and are present in both hepatocytes and hepatic non-parenchymal cells in the liver. The liver stem cells are a stem cell population that is responsible for liver regeneration when a tissue is damaged. The tissue fragment including liver stem cells is a tissue fragment of hepatocytes.

In Step A, the culturing is preferably performed by bringing the liver stem cells or the tissue fragment including liver stem cells and an extracellular matrix (ECM) into contact with each other.

Examples of a method of performing culturing by bringing the ECM and the liver stem cells or the tissue fragment including liver stem cells into contact with each other can include a method of mixing the liver stem cells or the tissue fragment including liver stem cells and an extracellular matrix precursor, allowing gelation of the extracellular matrix precursor to form the ECM, and then performing culturing by immersing the ECM in a growth medium.

As the ECM used in Step A, an ECM containing at least two types of specific glycoprotein is preferable. For example, the ECM may contain two different types of collagen or, contain collagen and laminin. The ECM may be a synthetic hydrogel extracellular matrix or a natural ECM. As the ECM, Matrigel (registered trademark) (BD Biosciences) containing laminin, entactin, and collagen IV is preferably used. Furthermore, a mixture of collagen I and Matrigel may also be used, and in this case, a mixing ratio is preferably 1:1 as a volume ratio. The extracellular matrix may be in a state of being coated onto a cell culture vessel or may be in a dissolved state.

A culture condition in Step A can be a condition that is generally adopted in culturing of animal cells. For example, the culturing can be performed in an environment in which a temperature is about 30° C. or higher and 40° C. or lower (preferably about 37° C.), and a $CO_2$ concentration is about 5% volume fraction (1 atmosphere).

Culture time can be appropriately adjusted according to the number of cells or a state of the cells. The proliferative liver organoid can be formed after an elapse of about 1 week or more and 2 weeks or less since the start of the culturing. It is particularly preferable that the culturing is performed for at least 2 weeks, from the viewpoints of proliferation of the proliferative liver organoid and formation of the organoid.

[Growth Medium]

The growth medium is a medium for culturing the proliferative liver organoid and contains an IL-6 family cytokine.

It is preferable that the growth medium does not substantially contain nicotinamide. Furthermore, in addition to the IL-6 family cytokine, it is preferable that the growth medium further contains a growth factor, a Wnt agonist, and a TGF-β inhibitor, and it is more preferable that the growth medium further contains a ROCK inhibitor, a BMP inhibitor, and forskolin.

The growth medium can be generally prepared by adding each component to a basal medium. Examples of the basal medium can include a Dulbecco's Modified Eagle's Medium (DMEM), a Minimum Essential Medium (MEM), KnockOut DMEM (KO-DMEM), a Glasgow Minimum Essential Medium (G-MEM), Basal Medium Eagle (BME), DMEM/Ham's F12, Advanced DMEM/Ham's F12 (Advanced DMEM/F12), an Iscove's modified Dulbecco's medium, Ham's F-10, Ham's F-12, Medium 199, and an RPMI 1640 medium.

Among the media, DMEM/F12 and RPMI 1640 to which HEPES, glutamine, and penicillin/streptomycin are added are preferable. Furthermore, Advanced DMEM/F12 or Advanced RPMI containing GlutaMAX (manufactured by GIBCO, L-alanyl-L-glutamine) instead of glutamine, which is optimized for serum-free culture, is preferable. It is preferable that glutamine and penicillin/streptomycin are added to the Advanced DMEM/F12 or Advanced RPMI medium.

Among various factors such as a cytokine or a growth factor that are involved in transition from the G0 phase to the G1 phase in the cell cycle, the inventors focused on an IL-6 family cytokine which is an inflammatory cytokine and found that a proliferative liver organoid that can be cultured for a long period of time while maintaining a high proliferative capacity can be obtained by using a growth medium containing the IL-6 family cytokine.

(1) IL-6 Family Cytokine

Examples of the IL-6 family cytokine can include interleukin-6 (IL-6), interleukin-11 (IL-11), oncostatin M (OSM), a leukemia inhibitory factor (LIF), cardiotrophin-1 (CT-1), and a ciliary neurotrophic factor (CNTF), and among these, IL-6 is preferable.

The source of the IL-6 family cytokine is not particularly limited, and IL-6 family cytokines derived from various organisms can be used. Among the IL-6 family cytokines, an IL-6 family cytokine derived from a mammal is preferable. Examples of the mammal can include a human, a mouse, a rat, a cow, a pig, a rabbit, and the like, and among these, a human is preferable.

Amino acid sequences of various components contained in the growth medium, including the IL-6 family cytokines of the major mammals, and base sequences of genes that code for the amino acid sequences can be acquired from, for example, a known database such as GenBank. For example, the amino acid sequence of human IL-6 is registered in GenBank under accession numbers XP_011513692 and XP_005249802.

The concentration of the IL-6 family cytokine contained in the growth medium is generally 10 ng/mL to 1.0 μg/mL, preferably 50 ng/mL to 500 ng/mL, and more preferably 80 ng/mL to 200 ng/mL.

(2) Nicotinamide

It is preferable that the growth medium does not substantially contain nicotinamide, from the viewpoint of enhancing and maintaining a cell proliferative capacity during long-term culture. Here, the expression "does not substantially contain nicotinamide" means that the growth medium does not contain nicotinamide at all (0 mM with respect to a total volume of the growth medium) or contains nicotinamide in a trace amount that does not hinder the enhancement and maintenance of the cell proliferative capacity during long-term culture, for example, at a concentration of 9 mM or lower, preferably 5 mM or lower, and more preferably 1 mM or lower.

(3) Growth Factor

It is preferable that the growth medium further contains a growth factor, from the viewpoint of enhancing cell proliferative properties. A growth factor refers to a diffusible signaling protein that stimulates cell growth, differentiation, survival, inflammation, and tissue repair.

Examples of the growth factor can include an epidermal growth factor (EGF), a fibroblast growth factor (FGF), a hepatocyte growth factor (HGF), amphiregulin, a heparin-binding EGF-like growth factor (HB-EGF), and the like.

EGF is one of the EGF family and is a growth factor that activates an epidermal growth factor receptor (EGFR or ErbB1). The activated EGFR mainly activates a MAPK signaling pathway and activates a PI3K signaling pathway or a Jak/stat signaling pathway.

The concentration of EGF contained in the growth medium is generally 10 ng/mL to 1,000 ng/mL, preferably 50 ng/mL to 500 ng/mL, and more preferably 80 ng/mL to 200 ng/mL.

HGF is a growth factor that activates a Met receptor, and the activated Met receptor activates an HGF-Met signaling pathway. The activation of the HGF-Met signaling pathway promotes a β-catenin pathway activation to promote angiogenesis or metalloprotease production.

The concentration of HGF contained in the growth medium is generally 10 ng/mL to 1,000 ng/mL, preferably 50 ng/mL to 500 ng/mL, and more preferably 80 ng/mL to 200 ng/mL.

FGF that can bind to the FGF receptor 2 (FGFR2) or the FGF receptor 4 (FGFR4) is preferable, FGF2, FGF4, FGF7 or FGF10 is more preferable, and FGF10 is particularly preferable.

The concentration of FGF contained in the growth medium is generally 20 ng/mL to 500 ng/mL, preferably 50 ng/mL to 300 ng/mL, and more preferably 80 ng/mL to 150 ng/mL.

Amphiregulin and HB-EGF are members of the EGF family and, like EGF, activate EGFR to activate a MAPK signaling pathway, a PI3K signaling pathway, or a Jak/stat signaling pathway.

The concentration of amphiregulin contained in the growth medium is generally 10 ng/mL to 1,000 ng/mL, preferably 50 ng/mL to 500 ng/mL, and more preferably 80 ng/mL to 200 ng/mL.

The final concentration of HB-EGF contained in the growth medium is generally 10 ng/mL to 1,000 ng/mL, preferably 50 ng/mL to 500 ng/mL, and more preferably 80 ng/mL to 200 ng/mL.

(4) Wnt Agonist

It is preferable that the growth medium further contains a Wnt agonist, from the viewpoints of maintaining the liver stem cells and enhancing the cell proliferative properties. The Wnt agonist is an agonist that activates a Wnt signaling pathway.

Examples of the Wnt agonist can include a Wnt family member, a R-spondin family member, norrin, and a glycogen synthase (GSK) inhibitor.

Examples of the Wnt family member can include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16, and among these, Wnt3a is preferable.

Since afamin is known to contribute to stabilization and solubilization of a Wnt family member, it is more preferable that a complex of the Wnt family member and afamin is used as the Wnt agonist. The complex of the Wnt family member and afamin can be used in a form of a mature culture solution (conditioned medium) containing the complex, in which the concentration of the Wnt family member is 18 ng/mL to 900 ng/mL.

Afamin refers to a glycoprotein belonging to the albumin family.

In GenBank, the amino acid sequence of human afamin is registered under AAA21612, and the amino acid sequence of bovine afamin is registered under DAA28569.

In a case where a conditioned medium in which the concentration of the Wnt family member is within the above range is used as the Wnt family member, the amount of the conditioned medium contained in the growth medium is generally 1 volume (v/v) % to 50 volume (v/v) %, preferably 10 volume (v/v) % to 30 volume (v/v) %, and more preferably 15 volume (v/v) % to 25 volume (v/v) %, with respect to the total volume of the growth medium.

Examples of the R-spondin family member can include R-spondin 1, R-spondin 2, R-spondin 3, and R-spondin 4, and among these, R-spondin 1 is preferable. When the R-spondin family member binds to Lgr5 in a cell membrane, Lgr5 is removed from the cell membrane by autoubiquitination. As a result, Frezzled which induces activation of the Wnt signaling pathway is stabilized in the cell membrane and activates the β-catenin pathway. The R-spondin family member can be used in a form of a mature culture solution containing the R-spondin family member, in which the concentration is 0.13 μg/mL to 6.5 μg/mL.

In a case where the conditioned medium in which the concentration of the R-spondin family member is within the above range is used as the R-spondin family member, a content of the conditioned medium contained in the growth medium is generally 1 volume (v/v) % to 50 volume (v/v) %, preferably 5 volume (v/v) % to 25 volume (v/v) %, and more preferably 8 volume (v/v) % to 20 volume (v/v) %, with respect to the total volume of the growth medium.

A GSK inhibitor refers to a glycogen synthase 3β (GSK3β) inhibitor. Since GSK3β phosphorylates β-catenin, thus promoting a degradation reaction thereof, the GSK inhibitor operates as a Wnt agonist.

Examples of the GSK inhibitor can include CHIR99021 (CAS number: 252917-06-9), SB216763 (CAS number: 280744-09-4), SB415286 (CAS number: 264218-23-7), CHIR98014 (CAS number: 252935-94-7), AZD1080 (CAS number: 612487-72-6), and LY2090314 (CAS number: 603288-22-8), and among these, CHIR99021 is preferable.

As the Wnt agonist, a combination of the Wnt family member and the R-spondin family member is preferably used, a combination of Wnt3a and R-spondin 1 is more preferably used, and a combination of a complex of Wnt3a and afamin and R-spondin 1 is even more preferably used.

(5) Rho Kinase Inhibitor

It is preferable that the growth medium further contains a Rho kinase (ROCK) inhibitor, from the viewpoint of inhibiting apoptosis. The ROCK inhibitor operates as an antagonist of IGF-1 signaling.

Examples of the ROCK inhibitor can include Y-27632 (CAS number: 146986-50-7), fasudil (CAS number: 105628-07-7), Y39983 (CAS number: 203911-26-6), Wf-536 (CAS number: 539857-64-2), SLx-2119 (CAS number: 911417-87-3), azabenzimidazole-aminofurazans (CAS number: 850664-21-0), DE-104, H-1152P (CAS number: 872543-07-6), Rho kinase α inhibitor (ROKα inhibitor), XD-4000, HMN-1152, 4-(1-aminoalkyl)-N-(4-pyridyl) cyclohexane-carboxamides, Rhostain, BA-210, BA-207, Ki-23095, and VAS-012. Among the ROCK inhibitors, Y-27632 is preferable.

The concentration of the ROCK inhibitor contained in the growth medium is generally 1 μM to 20 μM, preferably 5 μM to 15 μM, and more preferably 8 μM to 12 μM. Note that the unit "μM" indicates a concentration which is 1/1,000,000 of a molecular weight in 1 liter of the growth medium (mol/L), and the unit "μM" will have the same definition hereinafter.

(6) Transforming Growth Factor-β Inhibitor

It is preferable that the growth medium further contains a transforming growth factor (TGF)-β inhibitor, from the viewpoint of maintaining the liver stem cells. TGF-β inhibitor has an inhibitory activity of preferably 50% or higher, more preferably 70% or higher, even more preferably 80% or higher, and particularly preferably 90% or higher compared to a TGF-β activity level in the absence of the inhibitor. The TGF-β inhibitory activity can be evaluated by those skilled in the art according to a known method. Examples of such an evaluation system can include a cell assay in which cells are stably transfected with a reporter construct containing a human PAI-1 promoter or a Smad2/3 binding site that activates a luciferase reporter gene.

Examples of the TGF-β inhibitor can include A83-01 (CAS number: 909910-43-6), SB-431542 (CAS number: 301836-41-9), SB-505124 (CAS number: 694433-59-5), SB-525334 (CAS number: 356559-20-1), LY364947 (CAS number: 396129-53-6), SD-208 (CAS number: 627536-09-8), and SJN2511 (CAS number: 446859-33-2), and among these, A83-01 is preferable.

The concentration of the TGF-0 inhibitor contained in the growth medium is generally 0.05 μM to 50 μM, preferably 0.5 μM to 30 μM, and more preferably 1 μM to 15 μM.

(7) Bone Morphogenetic Protein Inhibitor

It is preferable that the growth medium further contains a bone morphogenetic protein (BMP) inhibitor, from the viewpoint of regulating the amount of the liver stem cells contained in the organoid.

BMP is a dimer ligand that binds to a receptor complex formed of type I and type II receptors which are two different receptor serine/threonine kinases. The type II receptor phosphorylates the type I receptor, resulting in activation of the receptor kinase. The type I receptor subsequently phosphorylates a specific receptor substrate (Smad1/5/9), resulting in induction of transcription activation by a signaling pathway.

Examples of the BMP inhibitor can include noggin, differential screening-selected gene aberrative in neuroblastoma (DAN), and a DAN-like protein. Examples of the DAN-like protein can include Cerberus and gremlin. Among the BMP inhibitors, noggin is preferable.

The concentration of the BMP inhibitor contained in the growth medium is generally 10 ng/mL to 100 ng/mL, preferably 15 ng/mL to 50 ng/mL, and more preferably 20 ng/mL to 30 ng/mL.

(8) Forskolin

It is preferable that the growth medium further contains forskolin, from the viewpoint of enhancing the cell proliferative properties.

The concentration of forskolin contained in the growth medium is generally 0.1 μM to 100 μM, preferably 1 μM to 50 μM, and more preferably 5 μM to 15 μM.

(9) Other Components

In addition to the above components, the growth medium can further contain at least one selected from the group consisting of gastrin, a neurobiological supplement, and N-acetylcysteine. Examples of the neurobiological supplement can include a supplement containing insulin, such as B27 Supplement (Thermo Fisher Scientific Solutions LLC) and N2 Supplement (Thermo Fisher Scientific Solutions LLC).

The amount of gastrin contained in the growth medium is generally 5 nM to 15 nM. Note that the unit "nM" indicates a concentration which is 1/1,000,000,000 of a molecular weight in 1 liter of the growth medium (mol/L), and the unit "nM" will have the same definition hereinafter.

B27 Supplement is a composition containing biotin, cholesterol, linoleic acid, linolenic acid, progesterone, putrescine, retinol, retinyl acetate, sodium selenite, triiodothyronine (T3), DL-α-tocopherol (vitamin E), albumin, insulin, transferrin, and the like, and is commercially available as a 50× liquid concentrate.

N2 Supplement is a composition containing 500 μg/mL human transferrin, 500 μg/mL bovine insulin, 0.63 μg/mL progesterone, 161 μg/mL putrescine, 0.52 μg/mL sodium selenite, and the like, and is commercially available as a 100× liquid concentrate.

The amount of N-acetylcysteine contained in the growth medium is generally 150 ng/mL to 250 ng/mL.

<Production Method for Metabolically Activated Liver Organoid>

In one embodiment, the present invention provides a production method including culturing the proliferative liver organoid produced by the production method for a proliferative liver organoid in a differentiation medium to obtain a metabolically activated liver organoid (hereinafter, referred to as "Step B"), in which the differentiation medium does not substantially contain an IL-6 family cytokine.

According to the production method for a metabolically activated liver organoid of the present embodiment, a metabolically activated liver organoid which is differentiated from the proliferative liver organoid produced by the production method for a proliferative liver organoid and has an excellent metabolic activity can be obtained. As shown in Examples described later, expressions of various metabolic enzymes in the metabolically activated liver organoid are improved to the extent that the organoid can be used in a pharmacokinetic study.

[Step B]

In Step B, the proliferative liver organoid produced by the above production method is differentiated into the metabolically activated liver organoid in the differentiation medium.

It is preferable that the proliferative liver organoid cultured for 2 weeks or more in Step A is used in Step B, from the viewpoints of proliferation of the proliferative liver organoid and formation of the organoid.

Culture period in Step B is generally 5 days to 15 days and preferably 7 days to 12 days.

In Step B, the culturing is preferably performed by bringing the proliferative liver organoid and an extracellular matrix (ECM) into contact with each other. For example, as shown in Examples described later, the proliferative liver organoid cultured in the growth medium layered onto a polymerized ECM may be physically dissociated as necessary so that an appropriate number of the proliferative liver organoids are contained and then cultured by layering the differentiation medium, instead of the growth medium.

Examples of the ECM used in Step B can include the ECM which is the same as that used in Step A described above.

Examples of a culture condition in Step B can include the culture condition which is the same as that in Step A.

In the production method for a metabolically activated liver organoid of the present embodiment, the differentiation of the proliferative liver organoid into the metabolically activated liver organoid can be determined or evaluated by using a hepatocyte marker expression, a drug-metabolizing activity, or the like as an index. Examples of the hepatocyte marker can include albumin (ALB), α-fetoprotein (AFP), tyrosine aminotransferase (TAT), the pregnane X receptor (PXR), and the like. The expression level of the hepatocyte marker may be measured at a gene level or at a protein level.

Examples of a method of obtaining cells only formed of the metabolically activated liver organoid from the cell population including the metabolically activated liver organoid can include a method of sorting and isolating the metabolically activated liver organoid using the presence of the hepatocyte marker as an index.

The drug-metabolizing activity can be evaluated by detection of a drug-metabolizing enzyme expression or a drug metabolism assay. Examples of the drug-metabolizing enzyme can include cytochrome P450 1A2 (CYP1A2), cytochrome P450 2B (CYP2B), cytochrome P450 2C9 (CYP2C9), cytochrome P450 2C19 (CYP2C19), cytochrome P450 2D6 (CYP2D6), cytochrome P450 2E1 (CYP2E1), cytochrome P450 3A4 (CYP3A4), cytochrome P450 3A7 (CYP3A7), uridine diphosphate-glucuronosyl-transferase (UGT), and sulfotransferase (SULT).

[Differentiation Medium]

The differentiation medium does not substantially contain the IL-6 family cytokine. Thus, the proliferative liver organoid can be differentiated into hepatocytes.

A differentiation medium that does not substantially contain nicotinamide is preferable, and a differentiation medium that contains a growth factor, a Wnt agonist, and a TGF-β inhibitor is preferable. It is preferable that the differentiation medium additionally contains a ROCK inhibitor, a BMP inhibitor, and forskolin.

The differentiation medium can generally be prepared by adding each component to a basal medium. Examples of the basal medium can include the minimum essential medium which is the same as that used for the growth medium.

(1) IL-6 Family Cytokine

The differentiation medium does not substantially contain the IL-6 family cytokine. The expression "does not substantially contain IL-6 family cytokine" means that the IL-6 family cytokine is contained in the differentiation medium at a concentration of 0 ng/mL or in a trace amount, specifically, at a concentration of lower than 10 ng/mL and preferably 1 ng/mL or lower. Examples of the IL-6 family cytokine can include those described above as the examples of the IL-6 family cytokine in the growth medium.

(2) Nicotinamide

It is preferable that the differentiation medium does not substantially contain nicotinamide, from the viewpoint of enhancing and maintaining a cell proliferative capacity during long-term culture. The expression "does not substantially contain nicotinamide" means that nicotinamide is contained in the differentiation medium at a concentration of 0 mM or in a trace amount, specifically, at a concentration of 9 mM or lower, preferably 5 mM or lower, and more preferably 1 mM or lower.

(3) Growth Factor

It is preferable that the differentiation medium further contains a growth factor, from the viewpoint of enhancing cell proliferative properties. The kind of the growth factor and the concentration of the growth factor contained in the differentiation medium are the same as those in the growth medium described above.

(4) Wnt Agonist

It is preferable that the differentiation medium further contains a Wnt agonist, from the viewpoints of maintaining the liver stem cells and enhancing the cell proliferative properties. The kind of the Wnt agonist and the concentration of the Wnt agonist contained in the differentiation medium are the same as those in the growth medium described above.

(5) ROCK Inhibitor

It is preferable that the differentiation medium further contains a ROCK inhibitor, from the viewpoint of inhibiting cell apoptosis. The kind of the ROCK inhibitor and the concentration of the ROCK inhibitor contained in the differentiation medium are the same as those in the growth medium described above.

(6) TGF-β Inhibitor

It is preferable that the differentiation medium further contains a TGF-β inhibitor, from the viewpoint of maintaining the liver stem cells. The kind of the TGF-β inhibitor and the concentration of the TGF-β inhibitor contained in the differentiation medium are the same as those in the growth medium described above.

(7) BMP Inhibitor

It is preferable that the differentiation medium further contains a BMP inhibitor, from the viewpoint of regulating the amount of the liver stem cells in the organoid. The kind of the BMP inhibitor and the concentration of the BMP inhibitor contained in the differentiation medium are the same as those in the growth medium described above.

(8) Forskolin

It is preferable that the differentiation medium further contains forskolin, from the viewpoint of enhancing the cell proliferative properties. The concentration of forskolin contained in the differentiation medium is the same as that in the growth medium described above.

(9) Notch Signaling Inhibitor

The differentiation medium can further contain a Notch signaling inhibitor and increase a CYP3A4 expression level in the metabolically activated liver organoid. Notch signaling is responsible for signal transduction between cells and controls cell differentiation.

Examples of the Notch signaling inhibitor can include a γ-secretase inhibitor such as L-685458 (CAS number: 292632-98-5), DAPT (CAS number: 208255-80-5), DBZ (CAS number: 209984-56-5), MRK560 (CAS number: 677772-84-8), 3,5-bis(4-nitrophenoxy)benzoic acid, MRK003 (CAS number: 623165-93-5), MK0752 (CAS number: 471905-41-6), flurbiprofen, and JLK6 (CAS number: 62252-26-0).

The concentration of the Notch signaling inhibitor contained in the differentiation medium is generally 10 ng/mL to 1,000 ng/mL, preferably 20 ng/mL to 500 ng/mL, and more preferably 30 ng/mL to 300 ng/mL.

(10) Vitamin D

The differentiation medium can further contain vitamin D and increase an albumin production amount in the metabolically activated liver organoid. Activation of a vitamin D receptor induces expressions of P21 and P27 proteins, thus arresting the G0/G1 phase in the cell cycle.

Vitamin D is synthesized and metabolized in the body. Thus, a vitamin D precursor, a vitamin D metabolite, and a vitamin D analogue are contained as vitamin D.

Examples of vitamin D can include a vitamin D precursor such as vitamin D2 (ergocalciferol), vitamin D3 (cholecalciferol), and 7-dehydrocholesterol, a vitamin D metabolite such as calcifediol and calcitriol, and a vitamin D analogue such as calcipotriol, 24,25-dihydroxyvitamin D3, ZK191784, and ZK2032788.

The concentration of vitamin D contained in the differentiation medium is generally 10 nM to 1,000 nM, preferably 50 nM to 800 nM, and more preferably 100 nM to 500 nM.

(11) DNA-Demethylating Agent

The differentiation medium can further contain a DNA-demethylating agent and increase the CYP3A4 expression level in the metabolically activated liver organoid.

Examples of the DNA-demethylating agent can include a cytidine analogue such as 5-aza-2-deoxycytidine, 5-azacytidine (azacitidine), zebularine, pseudoisocytidine, 5-fluoro-2-deoxycytidine, 5,6-dihydro-5-azacytidine, 2'-deoxy-5,6-dihydro-5-azacytidine, 6-azacytidine, 2',2'-difluoro-deoxycytidine, and cytosine-beta-D-arabinofuranoside.

The concentration of the DNA-demethylating agent contained in the differentiation medium is generally 0.1 μM to 100 μM, preferably 1 μM to 50 μM, and more preferably 5 μM to 15 μM.

(12) Other Additives

In addition to the above components, the differentiation medium can contain gastrin, B27 Supplement (Thermo Fisher Scientific Solutions LLC), N2 Supplement (Thermo Fisher Scientific Solutions LLC), or N-acetylcysteine. Gastrin, B27 Supplement (Thermo Fisher Scientific Solutions LLC), N2 Supplement (Thermo Fisher Scientific Solutions LLC), and N-acetylcysteine used in the differentiation medium and the concentrations thereof can be the same as those in the growth medium described above.

<Method of Inducing Metabolically Activated Liver Organoid into Proliferative Liver Organoid>

In one embodiment, the present invention provides an induction method including culturing the metabolically activated liver organoid produced by the production method for a metabolically activated liver organoid in an induction medium to induce the metabolically activated liver organoid into a proliferative liver organoid (hereinafter, referred to as "Step C"), in which the induction medium contains an IL-6 family cytokine.

According to the induction method of the present embodiment, the metabolically activated liver organoid can be turned back into a proliferative liver organoid, and the cell proliferative capacity can be restored.

The culture conditions in Step C are the same as the culture conditions in Step A in the production method for a proliferative liver organoid described above. Furthermore, the induction medium that is used has the same composition as that of the growth medium described in the production method for a proliferative liver organoid described above.

<Evaluation Method for Test Substance>

In one embodiment, the present invention provides an evaluation method for a test substance, the evaluation method including bringing the metabolically activated liver organoid produced by the production method for a metabolically activated liver organoid into contact with a test substance and evaluating a response of the metabolically activated liver organoid.

By using the evaluation method of the present embodiment, it is possible to evaluate metabolism, a drug interaction, hepatotoxicity, a transporter activity, and the like of the test substance in vitro and obtain a result close to a result obtained in in vivo evaluation.

Examples of the test substance can include a natural compound library, a synthetic compound library, a library of existing drugs, and a metabolite library. Organic compounds or inorganic compounds of various molecular sizes can be used as the test substance. Examples of the organic compounds can include a nucleic acid, a peptide, a protein, a lipid (a simple lipid, a complex lipid (a phosphoglyceride, a sphingolipid, glycosylglyceride, cerebroside, or the like), a prostaglandin, an isoprenoid, a terpene, a steroid), a polyphenol, catechin, a vitamin (B1, B2, B3, B5, B6, B7, B9, B12, C, A, D, E, or the like), and the like.

An existing component or a candidate component of a drug or a nutrition product is also one of the test substances. A plant extract, a cell extract, a culture supernatant, or the like can be used as the test substance. Furthermore, an interaction, a synergistic action, or the like between test substances can also be examined by adding two or more test substances at the same time.

The duration of allowing the contact between the test substance and the metabolically activated liver organoid is generally 10 minutes to 3 days and preferably 1 hour to 1 day. The performance of the contact between the test substance and the metabolically activated liver organoid can be divided into multiple steps.

The evaluation of a response of the metabolically activated liver organoid can be performed by, for example, mass spectrometry, liquid chromatography, or an immunological method, depending on a metabolite that is produced. Examples of the immunological method can include a fluoroimmunoassay method (a FIA method) and an enzyme immunoassay method (an EIA method).

Test substance metabolism can also be measured by using a drug-metabolizing enzyme (for example, cytochrome, UGT, or the like) expression in the metabolically activated liver organoid as an index. Examples of the drug-metabolizing enzyme expression can include an expression at an mRNA level or an expression at a protein level.

It is also possible to test toxicity of the test substance by the evaluation method of the present embodiment. For example, the toxicity of the test substance is evaluated by examining a state of the metabolically activated liver organoid after the contact between the metabolically activated liver organoid and the test substance. Examples of the state of the metabolically activated liver organoid can include viability, cell shape, the amount of a liver damage marker (for example, GOT, GPT, or the like) in the culture solution, and the like.

Other Embodiments

In one embodiment, the present invention provides a proliferative liver organoid produced by the production method for a proliferative liver organoid and a metabolically activated liver organoid produced by the production method for a metabolically activated liver organoid. The metabolically activated liver organoid of the present embodiment can be suitably used in in vitro evaluation of metabolism, a drug interaction, hepatotoxicity, a transporter activity, or the like of a test substance.

A difference in a gene expression pattern or the like may exist between the proliferative liver organoid and, for example, hepatocytes naturally existing in a living body and between the metabolically activated liver organoid and the hepatocytes naturally existing in a living body. However, it has not been determined whether or not such difference exists, and a significant amount of trial and error is required to be performed in order to identify such difference and specify the cell of the present embodiment by using the gene expression pattern or the like, which practically impossible. Therefore, it can be said that it is practical to specify the cell of the present embodiment by producing the cell by the production method described above.

In one embodiment, the present invention provides a growth medium and a differentiation medium. The growth medium and the differentiation medium are as described in the growth medium described in the production method for a proliferative liver organoid and the differentiation medium described in the production method for a metabolically activated liver organoid, respectively.

EXAMPLES

Hereinafter, the present invention will be described using Experimental Examples, but the present invention is not limited to the following Experimental Examples. Furthermore, all experiments were performed in accordance with an ethical research plan approved by Keio University School of Medicine Ethics Committee.

[Experimental Example 1] Production of Human Proliferative Liver Organoid

Cryopreserved primary human hepatocytes in suspension (Biopredic International, HEP187-S) were thawed in a water bath at 37° C., suspended in a 50 mL tube to which a serum-free medium was added, and subjected to centrifugation. Note that the serum-free medium is a medium obtained by adding HEPES, GlutaMAX, and penicillin/streptomycin to Advanced DMEM/F12. After the centrifugation, the supernatant was removed and then suspended in a serum-free medium, thereby preparing a hepatocyte suspension. 40,000 hepatocytes from the suspension were mixed with 50 µL of Matrigel (BD Biosciences), seeded in a 24-well tissue culture plate, and incubated at 37° C. for about 5 minutes or more and 10 minutes or less, until Matrigel completely polymerized. Subsequently, after the polymerization of Matrigel, a growth medium shown in Table 1 was layered thereon, and culturing was performed for 12 weeks, thereby producing a proliferative liver organoid of Experimental Example 1.

Note that R-spondin 1 is used in a form of a conditioned medium containing R-spondin 1, and a concentration of R-spondin 1 with respect to the total volume of the conditioned medium is 1.3 m/mL.

Similar to R-spondin 1, Wnt3a is used in a form of a conditioned medium containing a complex of Wnt3a and afamin, and a concentration of Wnt3a with respect to the total volume of the conditioned medium is 360 ng/mL.

The rate of proliferation of the proliferative liver organoid (two weeks after the start of the culture) from the cryopreserved primary hepatocytes in suspension was visually determined. The results are shown in Table 1. Determination criteria were (+++, ++, +, and −) in order from the highest proliferation rate.

The shape of the organoid was observed by observing the shape of the proliferative liver organoid two weeks after the start of the culture under a fluorescence microscope (manufactured by KEYENCE CORPORATION, apparatus name "BZ-X710"). An organoid with a hollow inside was determined to be "hollow", and an organoid with an inside filled with cells was determined to be "solid". The results are shown in Table 1. In addition, a microscope image is shown in FIG. 1.

Determination of whether or not maintenance and passaging of the proliferative liver organoid were possible was performed. For the determination, proliferation of the cells after the passaging was evaluated using a microscope image. The results are shown in Table 1.

Expression levels of mRNA of albumin, metabolic enzyme, and transporter genes were measured by extracting total ribonucleic acid (RNA) from the cells of the proliferative liver organoid two weeks after the start of the culture using a commercially available kit (product name "FastLane Cell cDNA Kit", QIAGEN), synthesizing cDNA, and performing real-time quantitative PCR. The real-time quantitative PCR was performed using a commercially available kit (product name "SYBR (registered trademark) Premix Ex Taq (Perfect Real Time)", Takara Bio Inc.). Furthermore, the measurement results were corrected using glyceraldehyde-3-phosphate dehydrogenase (GAPDH) as an internal control. The results are shown in Table 3. Note that the numerical values in Table 3 indicate relative values obtained when the expression levels in the cryopreserved primary human hepatocytes in suspension (Biopredic International, HEP187-S) are assumed to be 100.

Figure 2:
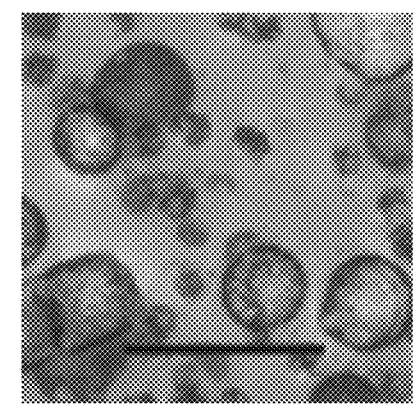
FIG. 2 is a microscope image of liver organoids in Experimental Example 2. The scale bar is 100 μm.

[Experimental Example 2 to Experimental Example 4] Production of Liver Organoids Liver organoids were produced using the same method as that in Experimental Example 1, except for using growth media each having a composition shown in Table 1. Proliferation rates, cell shapes, maintenance and expansion culturing, and expression levels of metabolic enzymes, transporters, and albumin at a gene level were also measured using the same methods as those in Experimental Example 1. The results are shown in Table 1 and Table 3. In addition, a microscope image of the liver organoid of Experimental Example 2 is shown in FIG. 2.

[Experimental Example 5] Production of Metabolically Activated Liver Organoid

Figure 3:
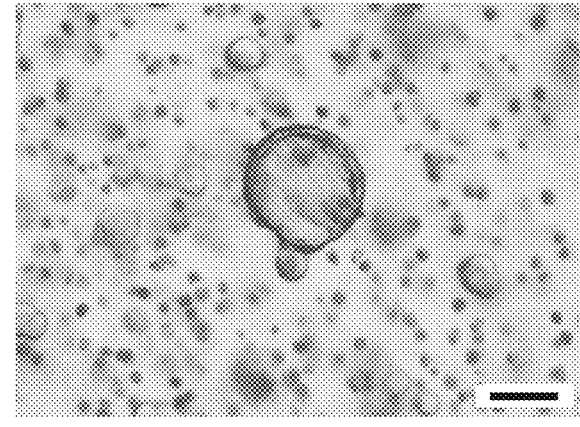
FIG. 3 is a microscope image of metabolically activated liver organoids in Experimental Example 5.
Figure 4A:
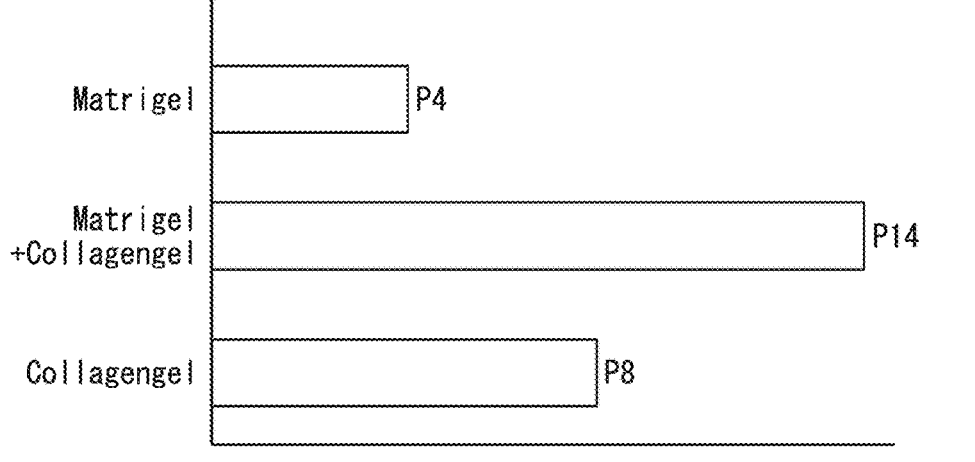
FIG. 4A is a graph showing comparison of passage numbers in cases of using Matrigel, a mixture of collagen and Matrigel, and collagen as extracellular matrices in Experimental Example 13. P in FIG. 4A indicates a passage number.
Figure 4B:
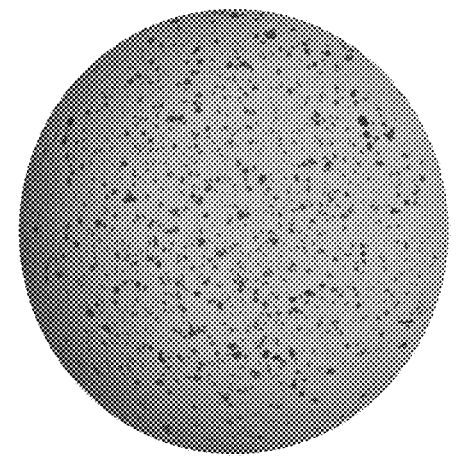
FIG. 4B is a microscope image of proliferative liver organoids at day 190 of culture, which are at passage 14, in the case of using the mixture of collagen and Matrigel as an extracellular matrix in Experimental Example 13.
Figure 4C:
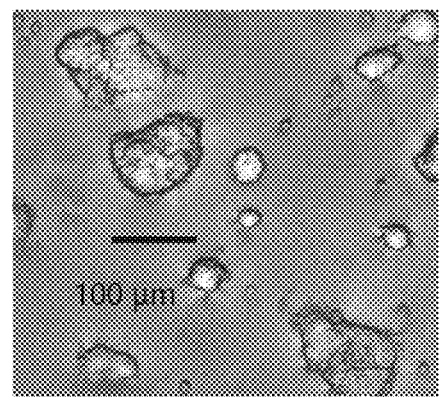
FIG. 4C is an enlarged image of FIG. 4B. The scale bar is 100 μm.
Figure 4D:
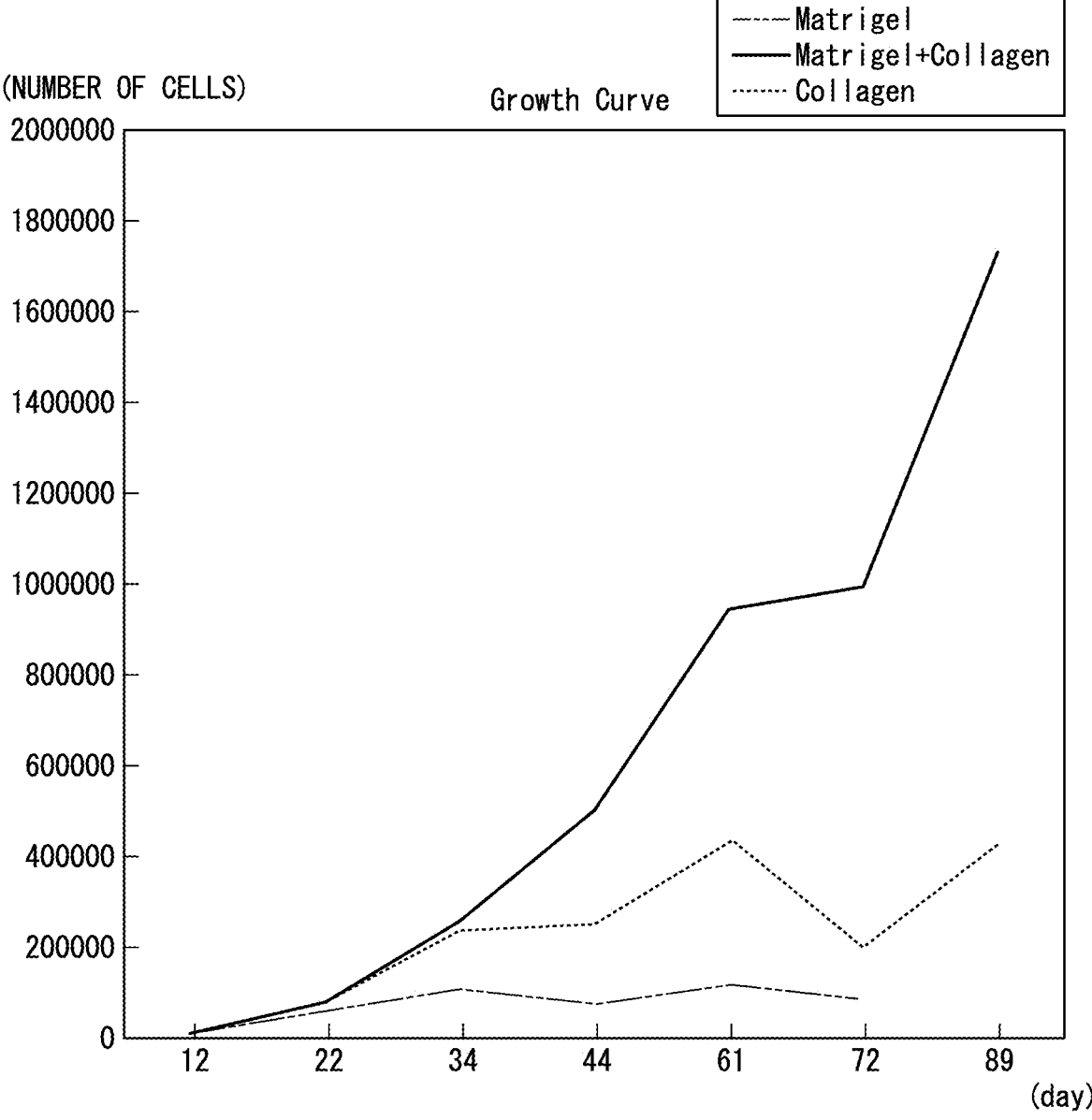
FIG. 4D is a graph showing comparison of proliferative capacities in the cases of using Matrigel, the mixture of collagen and Matrigel, and collagen as the extracellular matrices in Experimental Example 13.

The human proliferative liver organoid cultured in a growth medium for two weeks using the same method as that in Experimental Example 1 was diluted by mechanical dissociation and passaged. At this time, the medium was changed from the growth medium to a differentiation medium, and the organoid was cultured for one week, thereby producing a metabolically activated liver organoid. As the differentiation medium, a serum-free medium having the composition shown in Table 2 and not containing IL-6 was used. A cell shape, maintenance and expansion culturing, and expression levels of metabolic enzymes, transporters, and albumin at a gene level were measured using the same methods as those in Experimental Example 1. The results are shown in Tables 2 and 3. In addition, a microscope image of the obtained liver organoid is shown in FIG. 3.

[Reference Example 1] Production of Human Liver Organoid

A human liver organoid was produced using the method described in Non-Patent Document 2. Expression levels of metabolic enzymes, transporters, and albumin at a gene level were measured using the same methods as those in Experimental Example 1. The results are shown in Table 3.

TABLE 1

|  | Composition | Experimental Example 1 | Experimental Example 2 | Experimental Example 3 | Experimental Example 4 |
|---|---|---|---|---|---|
| Growth medium | R-Spondin 1 | 10% (v/v) | 10% (v/v) | 10% (v/v) | 15% (v/v) |
|  | Wnt3a | 20% (v/v) | 20% (v/v) | 20% (v/v) | — |
|  | CHIR99021 | — | — | — | 3 μM |
|  | Noggin | 25 ng/ml | 25 ng/ml | 25 ng/ml | — |
|  | Nicotinamide | — | — | 10 mM | 10 mM |
|  | EGF | 50 ng/ml | 50 ng/ml | 50 ng/ml | 50 ng/ml |
|  | FGF7 | — | — | — | 100 ng/ml |
|  | FGF10 | 100 ng/ml | 100 ng/ml | 100 ng/ml | 100 ng/mL |
|  | TGFα | — | — | — | 20 ng/mL |
|  | HGF | 50 ng/mL | 50 ng/mL | 50 ng/ml | 50 ng/mL |

TABLE 1-continued

| Composition | Experimental Example 1 | Experimental Example 2 | Experimental Example 3 | Experimental Example 4 |
|---|---|---|---|---|
| Y-27632 | 10 μM | 10 μM | 10 μM | 10 μM |
| Forskolin | 10 μM | 10 μM | 10 μM | — |
| A83-01 | 5 μM | 5 μM | 5 μM | 2 μM |
| IL-6 | 100 ng/ml | — | — | — |
| Proliferative liver organoid proliferation rate | +++ | +++ | + | + |
| Cell shape | Hollow | Solid | Solid | Solid |
| Maintenance and expansion culturing | Possible | Not possible | Not possible | Not possible |

TABLE 2

| | Composition | Experimental Example 5 |
|---|---|---|
| Differentiation medium | R-Spondin 1 | 10% (v/v) |
| | Wnt3a | 20% (v/v) |
| | CHIR99021 | — |
| | Noggin | 25 ng/ml |
| | Nicotinamide | — |
| | EGF | 50 ng/mL |
| | FGF7 | — |
| | FGF10 | 100 ng/mL |
| | TGFα | — |
| | HGF | 50 ng/ml |
| | Y-27632 | 10 μM |
| | Forskolin | 10 μM |
| | A83-01 | 5 μM |
| | IL-6 | — |
| Cell shape | | Hollow |
| Maintenance and expansion culturing | | Not possible |

TABLE 3

| Gene | Experimental Example 1 | Experimental Example 5 | Experimental Example 2 | Reference Example 1 |
|---|---|---|---|---|
| Type | Proliferative liver organoid | Metabolically activated liver organoid | Liver organoid | Human liver organoid |
| CYP1A2 | 16.6 | 101.4 | 107.2 | 1.5 |
| CYP2C9 | 10.5 | 22.5 | 11.3 | 0.8 |
| CYP2C19 | 10.0 | 13.9 | 68.3 | 9.3 |
| CYP2D6 | 12.9 | 29.5 | 30.6 | 0.6 |
| CYP2E1 | 161.3 | 320.4 | 234.6 | 0.05 |
| CYP3A4 | 0.4 | 10.1 | 3.3 | 1.9 |
| UGT1A1 | 160.2 | 353.1 | 220.4 | 29.7 |
| UGT2B7 | 8.7 | 28.7 | 36.9 | 2.2 |
| SULT1A1 | 12.0 | 28.7 | 18.3 | 23.8 |
| P-gp | 82.4 | 90.8 | 65.1 | Measurement was not performed |
| MRP2 | 92.0 | 741.3 | 114.1 | Measurement was not performed |
| Albumin | 26.2 | 70.2 | 38.4 | 0.8 |
| Lgr5 | 56.3 | 204.2 | Measurement was not performed | N.D. | obtained using the growth media that contained nicotinamide, but did not contain IL-6, (Experimental Example 3 and Experimental Example 4) had solid cell shapes and low proliferation rates, and maintenance and expansion culturing thereof was not possible.

As shown in Table 2 and Table 3, the metabolically activated liver organoid of Experimental Example 5 differentiated from the proliferative liver organoid of Experimental Example 1 using the differentiation medium not containing IL-6 had a hollow cell shape, and although maintenance and expansion culturing thereof was not possible, the expression levels of the metabolic enzymes, the transporters, and albumin at a gene level all improved to the extent that the organoid was able to be used in a pharmacokinetic study. Furthermore, from the microscope image of FIG. 3, it was observed that a yellow component which was presumed to be bilirubin was contained inside the organoid.

As shown in Table 1, the proliferative liver organoid obtained using the growth medium containing L-6 (Experimental Example 1) had a hollow cell shape and a high proliferation rate, and maintenance and expansion culturing thereof was possible. Furthermore, from the microscope image of FIG. 1, it was observed that a red component was contained inside the organoid.

On the other hand, the liver organoid obtained using the growth medium not containing IL-6 (Experimental Example 2) had a solid cell shape, and although the proliferation rate thereof was high, maintenance and expansion culturing thereof was not possible. Furthermore, the liver organoids

[Experimental Example 6 and Experimental Example 7] Production of Proliferative Liver Organoids Proliferative liver organoids were produced using the same method as that in Experimental Example 1, except for using growth media shown in Table 4. Proliferation rates and maintenance and expansion culturing were also measured using the same methods as those in Experimental Example 1. The results are shown in Table 4.

TABLE 4

| | Composition | Experimental Example 1 | Experimental Example 6 | Experimental Example 7 |
|---|---|---|---|---|
| Growth medium | R-Spondin 1 | 10% (v/v) | 10% (v/v) | 10% (v/v) |
| | Wnt3a | 20% (v/v) | 20% (v/v) | 20% (v/v) |
| | Noggin | 25 ng/mL | 25 ng/mL | 25 ng/ml |
| | EGF | 50 ng/ml | 50 ng/ml | 50 ng/ml |
| | FGF10 | 100 ng/ml | 100 ng/mL | 100 ng/mL |
| | HGF | 50 ng/mL | 50 ng/ml | 50 ng/ml |
| | Y-27632 | 10 μM | 10 μM | 10 μM |
| | Forskolin | 10 μM | 10 μM | 10 μM |
| | A83-01 | 5 μM | 5 μM | 5 μM |
| | IL-6 | 100 ng/mL | 100 ng/mL | 100 ng/ml |
| | Amphiregulin | — | 100 ng/ml | — |
| | HB-EGF | — | — | 100 ng/mL |
| Proliferative liver organoid proliferation rate | | ++ | +++ | +++ |
| Maximum period of maintenance and expansion culturing | | 12 weeks | 14 weeks | 14 weeks |

[Experimental Example 8 to Experimental Example 12] Production of Metabolically Active Liver Organoids Metabolically active liver organoids were produced using the same method as that in Experimental Example 5, except for using differentiation media shown in Table 4. Albumin expression levels and CYP3A4 expression levels were also measured using the same method as that in Experimental Example 5. The results are shown in Table 5.

TABLE 5

| | Composition | Experimental Example 8 | Experimental Example 9 | Experimental Example 10 | Experimental Example 11 | Experimental Example 12 |
|---|---|---|---|---|---|---|
| Differentiation medium | R-Spondin 1 | 10% (v/v) | 10% (v/v) | — | 10% (v/v) | 10% (v/v) |
| | Wnt3a | 20% (v/v) | 20% (v/v) | — | 20% (v/v) | 20% (v/v) |
| | Noggin | 25 ng/ml | 25 ng/ml | 25 ng/ml | 25 ng/ml | 25 ng/ml |
| | EGF | 50 ng/mL | 50 ng/mL | 50 ng/mL | 50 ng/ml | 50 ng/ml |
| | FGF10 | 100 ng/ml | 100 ng/ml | 100 ng/ml | 100 ng/ml | 100 ng/ml |
| | HGF | 50 ng/ml | 50 ng/ml | 50 ng/ml | 50 ng/ml | 50 ng/ml |
| | Y-27632 | 10 μM | 10 μM | 10 μM | 10 μM | 10 μM |
| | Forskolin | 10 μM | 10 μM | 10 μM | 10 μM | 10 μM |
| | A83-01 | 5 μM | 5 μM | 5 μM | 5 μM | 5 μM |
| | IL-6 | — | — | — | — | — |
| | DAPT | — | 100 ng/mL | 100 ng/ml | — | — |
| | Calcitriol | — | — | — | 25—0 nM | — |
| | Azacitidine | — | — | — | — | 10 μM |
| Albumin expression level | | 1 | 0.8 | 1.8 | 13.6 | N.D. |
| CYP3A4 expression level | | 1 | 24.1 | 15 | 6 | 4 |

[Experimental Example 13] Production of Human Proliferative Liver Organoid on Collagen-Matrigel Cryopreserved primary human hepatocytes in suspension (Biopredic International, HEP187-S) were thawed in a water bath at 37° C., suspended in a 50 mL tube to which a serum-free medium was added, and subjected to centrifugation. Note that the serum-free medium is a medium obtained by adding HEPES, GlutaMAX, and penicillin/streptomycin to Advanced DMEM/F12. After the centrifugation, the supernatant was removed and then suspended in a serum-free medium, thereby preparing a hepatocyte suspension. 50,000 hepatocytes from the suspension were mixed with 12.5 μL of Matrigel (BD Biosciences) and 12.5 μL of collagen I (Nitta Gelatin Inc.), seeded in a 48-well tissue culture plate, and incubated at 37° C. for about 5 minutes or more and 10 minutes or less, until Matrigel and the collagen I completely polymerized. A control was also prepared by using only Matrigel or only the collagen. Subsequently, after the polymerizations of Matrigel and the collagen I, the growth medium shown in Table 1 above was layered thereon, and culturing was performed, thereby producing a proliferative liver organoid of Experimental Example 13.

As shown in FIG. 4A to FIG. 4D, in a case where ECM obtained by mixing the collagen and Matrigel was used, culturing at a higher passage number was possible, and enhancement of proliferation was observed.

What is claimed is:

1. A method for producing a metabolically activated liver organoid, the method comprising:

culturing primary human hepatocytes or cryopreserved primary human hepatocytes in a growth medium and with contact to an extracellular matrix to obtain a proliferative liver organoid for at least 10 days and up to 14 days; and culturing the proliferative liver organoid in a differentiation medium for 1 week to obtain a metabolically activated liver organoid, wherein the growth medium comprises an interleukin-6 family cytokine, at least one growth factor, a Wnt agonist, a transforming growth factor-β inhibitor, a bone morphogenetic protein inhibitor, and a forskolin, wherein the interleukin-6 family cytokine comprises at least one selected from the group consisting of inter-leukin-6, interleukin-11, oncostatin M, a leukemia inhibitory factor, cardiotrophin-1, and a ciliary neuro-trophic factor, wherein the differentiation medium comprises a growth factor, a transforming growth factor-β inhibitor, and a forskolin, and the differentiation medium does not substantially contain an interleukin-6 family cytokine, wherein the extracellular matrix comprises basement membrane matrix, collagen I, or a 1:1 mixture of collagen I and basement membrane matrix, and wherein the at least one growth factor in the growth medium is selected from the group consisting of:

epidermal growth factor;

hepatocyte growth factor;

heparin-binding EGF-like growth factor;

amphiregulin;

a combination of epidermal growth factor, fibroblast growth factor 10, and hepatocyte growth factor;

a combination of epidermal growth factor and fibro-blast growth factor 10;

a combination of hepatocyte growth factor and fibro-blast growth factor 10; and a combination of epidermal growth factor and hepato-cyte growth factor.

2. The method according to claim 1, wherein the growth medium does not substantially con-tain nicotinamide.

3. The method according to claim 1, wherein the growth factor in the growth medium further comprises at least one selected from the group consist-ing of an epidermal growth factor, a fibroblast growth factor, a hepatocyte growth factor, amphiregulin, and a heparin-binding EGF-like growth factor.

4. The method according to claim 1, wherein the growth medium further comprises a Rho kinase inhibitor.

5. The method according to claim 1, wherein the differentiation medium does not substantially contain nicotinamide.

6. The method according to claim 1, wherein the growth factor in the differentiation medium comprises at least one selected from the group consist-ing of an epidermal growth factor, a fibroblast growth factor, and a hepatocyte growth factor.

7. The method according to claim 1, wherein the differentiation medium further comprises a Wnt agonist.

8. The method according to claim 1, wherein the differentiation medium further comprises a Rho kinase inhibitor.

9. The method according to claim 1, wherein the differentiation medium further comprises a bone morphogenetic protein inhibitor.

10. The method according to claim 1, wherein the differentiation medium further comprises vitamin D.

11. The method according to claim 1, wherein the differentiation medium further comprises a Notch inhibitor.

12. The method according to claim 1, wherein the extra-cellular matrix comprises collagen I.

13. The method according to claim 1, wherein the extra-cellular matrix comprises laminin, entactin, and collagen IV.

* * * * *